United States Patent [19]

Huber et al.

[11] Patent Number: 6,090,975

[45] Date of Patent: Jul. 18, 2000

[54] PROCESS FOR THE PREPARATION OF 2-ACETYLCARBOXYLIC ESTERS

[75] Inventors: Wolfgang Huber, Salzburg; Günter Eichberger, Weisskirchen; Harald Pöschko, Ennsdorf; Gerhard Burschik, Linz, all of Austria

[73] Assignee: DSM Fine Chemicals Austria GmbH, Austria

[21] Appl. No.: 09/222,349

[22] Filed: Dec. 29, 1998

[30] Foreign Application Priority Data

Dec. 29, 1997 [AT] Austria .................................. 2193/97

[51] Int. Cl.$^7$ ..................................................... C07C 69/72
[52] U.S. Cl. ............................................................. 560/178
[58] Field of Search ............................................. 560/178

[56] References Cited

U.S. PATENT DOCUMENTS

| 3,839,418 | 10/1974 | Hinton et al. | 560/174 |
| 4,220,799 | 9/1980 | Berthold et al. | 560/126 |
| 5,786,501 | 7/1998 | Jackson | 560/178 |
| 5,811,573 | 9/1998 | Nishihira et al. | 560/146 |

FOREIGN PATENT DOCUMENTS 1340182  12/1973  United Kingdom .

*Primary Examiner*—Rosalynd Keys

[57] ABSTRACT

Process for the preparation of 2-acetylcarboxylic esters by reacting an acetoacetic ester having 1 to 6 C atoms in the alkyl moiety with an aliphatic aldehyde having 1 to 12 C atoms at 0 to 40° C. in the presence of a condensation catalyst, subsequently removing the water of reaction formed and unreacted starting materials and then hydrogenating the material at 20–160° C., the temperature in the first hydrogenation phase being between 20 and 90° C. and the temperature in the second phase being increased to 50 to 160° C., depending on the starting temperature.

8 Claims, No Drawings

PROCESS FOR THE PREPARATION OF 2-ACETYLCARBOXYLIC ESTERS

Acetylcarboxylic esters are used for making a multiplicity of highly diverse products such as, for example, fungicides or insecticidal pyrimidine compounds, pancreas lipase inhibitors or perfume products.

A plurality of synthetic routes for preparing acetylcarboxylic esters have already been described in the literature. One possible variant is the reaction of acetoacetic esters with an alkyl bromide or alkyl iodide. In this variant, however, dialkylated compounds or O-alkylacetoacetic esters, which cannot be removed from the desired end products by distillation, are readily formed. An alternative method is a one-pot reaction, in which the acetoacetic ester and an aldehyde undergo a condensation reaction and the resulting reaction mixture is hydrogenated to give the desired end product, without the intermediate formed being isolated. This reaction, however, yields a multiplicity of secondary compounds such as, for example, condensates and the like. Moreover, the acetylcarboxylic ester yield is unsatisfactory (<40%).

It was therefore an object of the invention to find an improved process for the preparation of 2-acetylcarboxylic esters which yields the desired ester in high yields and in high purity while avoiding the formation of secondary products due to condensation.

Accordingly, the invention relates to an improved process for the preparation of 2-acetylcarboxylic esters by reacting an acetoacetic ester with an aldehyde, followed by hydrogenation, which comprises a) reacting an acetoacetic ester having 1 to 6 C atoms in the alkyl moiety with an aliphatic aldehyde having 1 to 12 C atoms at 0 to 40° C. in the presence of a condensation catalyst, b) removing, after condensation, the water of reaction formed and unreacted starting materials from the reaction mixture, subsequently c) hydrogenating the remaining residue in substance at 20 to 160° C. and a pressure of 1 to 100 bar in the presence of a hydrogenation catalyst, the temperature in the first hydrogenation phase being between 20 and 90° C. and the temperature in the second phase being increased to 50 to 160° C., depending on the starting temperature, d) and subsequently isolating the 2-acetylcarboxylic ester in question from the reaction mixture by distillation.

In accordance with step a) of the process according to the invention, an acetoacetic ester and an aldehyde are subjected to a condensation reaction. Suitable acetoacetic esters are those esters which have 1 to 6 C atoms in the alkyl moiety. Examples are methyl, ethyl, propyl, iso-propyl, n-butyl, pentyl or hexyl esters of acetoacetic acid. $C_1$ to $C_3$ esters are preferably employed. The aldehydes used are aliphatic aldehydes having 1 to 12 C atoms. Aliphatic aldehydes are straight-chain, branched or cyclic aldehydes which can be saturated but also mono- or polyunsaturated. If an unsaturated aldehyde is employed, it must be borne in mind that the multiple bonds are reduced when the subsequent hydrogenation takes place. Furthermore, the aldehyde may be unsubstituted or substituted by groups which are inert under the reaction conditions, such as, inter alia, phenyl groups, substituted phenyl groups, halogen groups, nitro groups, alkoxy groups or heterocycles.

Examples are, inter alia, formaldehyde as such or in a polymeric form, acetaldehyde, n-butyraldehyde, isobutyraldehyde, propionaldehyde, valeraldehyde, caproaldehyde, octanal, dodecanal, decanal and 2-propenal.

Saturated aliphatic aldehydes having 2 to 10 C atoms, especially preferably having 3 to 8 C atoms, are preferably used.

In the process according to the invention, aldehyde and ester are preferably reacted in equimolar quantities or with an excess of ester, since an excess of aldehyde may lead to aldol addition reactions.

Condensation is effected in the presence of a condensation catalyst. Suitable for this purpose are all catalysts which are conventionally used for condensation reactions of aldehydes.

Examples are basic catalysts such as, inter alia, ammonia or amines, for example piperidine, pyridine, substituted pyridines, morpholine, diethylamine and diethanolamine, all of which may exist in the form of salts with organic acids such as acetic acid, butyric acid or oxalic acid, such as, inter alia, piperidine acetate.

Other suitable catalysts are, for example, other basic salts such as sodium acetate or basic ion-exchange resins and acidic catalysts such as, inter alia, zinc acetate and magnesium chloride.

Amines or salts thereof are preferably employed as catalysts. Piperidine, piperidine acetate, pyridine or morpholine are especially preferably used.

The required amount of catalyst depends on the type of catalyst. Basic catalysts are employed according to the invention in amounts of between 0.1 and 3.0 mol %, preferably between 0.2 and 2 mol %, while acidic catalysts are preferably added in slightly larger amounts.

If appropriate, the catalyst can be employed in combination with a diluent, such as methanol, ethanol or acetic acid.

The condensation reaction is carried out at temperatures of 0 to 40° C., preferably 0 to 20° C.

The starting materials and the catalyst may be metered in in any desired sequence.

It is preferred initially to introduce the ester and the aldehyde and to meter in the catalyst slowly. Since, at the beginning, the reaction rate is extremely high and the reaction is strongly exothermic, the reaction mixture must be cooled sufficiently so that the reaction temperature does not climb beyond 40° C., preferably not beyond 20° C.

If appropriate, after metered addition has ended, the mixture is stirred for a further 10 to 120 minutes, preferably 30 to 90 minutes, at 0 to 40° C., preferably at 10 to 20° C., to complete condensation.

In accordance with step b), the water of reaction formed and excess, unreacted starting material is subsequently removed from the reaction mixture.

In this step it is essential to keep the temperature in the reaction vessel as low as possible to avoid undesired secondary reactions. In the event that the starting materials are insoluble in water, the mildest way of removing the water of reaction from the reaction mixture is phase separation at 15 to 35° C., preferably at room temperature. Residual traces of water can be distilled off under the mildest possible conditions after phase separation, together with the unreacted starting materials. However, the water may also be distilled off at once, without prior phase separation, together with the unreacted starting materials. The mildest possible distillation conditions are achieved when the residence time is short, preferably less than 1 minute. Preferred methods are short-path or thin-film evaporators. It is especially preferred continuously to strip the water of reaction and excess starting materials from the reaction mixture.

The resulting distillate forms two phases, so that the starting materials can readily be separated from the water of reaction and re-employed.

The bottom product which remains after removal of the water of reaction and the excess starting materials contains the corresponding 2-acetylalkenoic ester, which is hydrogenated in step c). To this end, the bottom product is introduced into a suitable apparatus, treated with a hydrogenation catalyst and hydrogenated at 20 to 160° C. and a pressure of 1 to 100 bar. Hydrogenation is preferably effected at 5 to 30 bar. Suitable hydrogenation catalysts are customary hydrogenation catalysts such as palladium, platinum, rhodium, cobalt or ruthenium on silicon dioxide, on aluminum oxide or on carbon, and also Raney nickel catalysts. Palladium on aluminum oxide or on carbon is preferably used. The hydrogenation catalyst is added in an amount of 0.05 to 0.5% by weight, based on 2-acetyl-2-alkenoic ester.

The first phase of the hydrogenation is preferably carried out at low temperatures, for example at 20 to 90° C. After approximately 5 to 120 minutes, preferably after 10 to 80 minutes, the temperature is slowly increased and the reaction mixture is subjected to a post-hydrogenation.

The temperature at which this is done is increased to 50 to 160° C., preferably to 80 to 150° C., depending on the starting temperature in the first hydrogenation phase. During this time, stirring of the reaction mixture is continued until the uptake of hydrogen has ended. This second hydrogenation phase guarantees that secondary products formed by Michael addition are thermally recleaved.

After the hydrogenation step, the resulting reaction mixture is cooled to room temperature, the catalyst is filtered off and the ester in question is isolated from the mixture by distillation.

The process according to the invention allows the 2-acetylcarboxylic esters in question to be prepared without further purification in high yields of over 80% by weight and a purity of over 98%.

The 2-acetylcarboxylic esters prepared in accordance with the present process are distinguished by a negligibly small content of impurities such as condensation products and thermal decomposition products, so that these products are outstandingly suitable for the preparation of, for example, oxetanones, which are used as pancreas lipase inhibitors, and for the preparation of fungicidal or insecticidal pyrimidine compounds or for the preparation of perfume products.

EXAMPLE 1

696.8 g (6.0 mol) of methyl acetoacetate and 601.0 g (6.0 mol) of hexanal were introduced into a 2 l reaction vessel, the mixture being cooled to 5° C. 6.5 g (0.076 mol) of piperidine were subsequently metered in with cooling and stirring in the course of 15 minutes. The water of reaction formed and unreacted hexanal and acetoacetate were subsequently distilled off at 20 mbar using a distillation bridge (bottom temperature: 20–150° C.).

This gave 1059.7 g of methyl acetyloctenoate as bottom product and 244.2 g of unreacted starting materials and water of reaction in the distillate.

330 g of the methyl acetyl-2-octenoate prepared above (bottom product) were then introduced into a 1-liter stirred autoclave, treated with 0.33 g of 5% palladium/active charcoal as catalyst and hydrogenated for 10 minutes at 90° C. and 15 bar.

The reaction mixture was subsequently slowly heated to 150° C. and stirred at this temperature until hydrogen uptake had ended.

After hydrogenation, the reaction mixture was cooled to room temperature, the catalyst was filtered off and the filtrate distilled through a bubble-cap column (6 trays, diameter 3 cm, length 35 cm) at 5 mbar.

The first runnings were removed at a reflux ratio of 5:1 (5 reflux/1 distillate), the main fraction at a reflux ratio of 3:1.

| First runnings | (22–121° C.) 36.1 g |
| --- | --- |
| Main fraction | (120–123° C.) |
| Yield: | 240.9 g methyl acetyloctanoate |
|  | (= 64.5% of theory) |
| Purity (GC): | 98.2% |
| Bottom product: | 41.9 g |

After the water of reaction had been removed, the unreacted starting materials which had been distilled off were recirculated for a further batch and re-employed, thus achieving an increased yield of 76%.

EXAMPLE 2

A total of 7 batches were produced by the same procedure. In each case, methyl acetoacetate (AEE) and hexanal (HEX) were introduced and cooled to approx. 8° C. with sodium chloride solution. Then, all of the catalyst (piperidine PIP) was added in the course of 2 minutes. During the entire reaction, the reactor was cooled with sodium chloride solution. After addition of the catalyst, the reactor temperature climbed to a maximum of between 30 and 40° C. in the course of minutes and then dropped back to 14° C. in the course of one hour, due to cooling with sodium chloride solution. The detailed feeds and temperatures can be found in Table 1.

In batches 4 to 7, the feed additionally included a recyclate. The recyclate was obtained by distilling off the unreacted starting materials from the previous batch in question after condensation has taken place.

TABLE 1

| Batch | AEE (kg) | HEX (kg) | PIP (l) | Recyclate (kg) | (° C.) start | max. |
| --- | --- | --- | --- | --- | --- | --- |
| 1 | 3487 | 3274 | 37 | — | 16 | 39 |
| 2 | 3488 | 3273 | 30 | — | 11 | 37 |
| 3 | 3486 | 3266 | 30 | — | 11 | 35 |
| 4 | 1420 | — | 20 | 4740 | 10 | 25 |
| 5 | 1678 | 291 | 20 | 5580 | 10 | 27 |
| 6 | 2027 | 1489 | 20 | 2973 | 10 | 30 |
| 7 | 1597 | 667 | 20 | 3000 | 9 | 36 |

A methyl 2-acetyloctenoate (ACOEM) content of 50–60% with 0.1 to 0.2% by weight of condensate was found after a reaction time of as little as 5 minutes.

After a reaction time of approx. 6 hours, 60–70% by weight of ACOEM with 0.4–0.6% by weight of condensate were obtained in each case.

The unreacted starting materials and the water of reaction were distilled off on the short-path evaporator.

| Feed rate: | 500 l/h |
| --- | --- |
| Heating steam pressure: | 2 bar |
| Vacuum: | 40 mbar |
| Bottom product: | 60% |

Result product quality in GC area percent

|  | ACOEM | AEE | HEX | Condensate |
|---|---|---|---|---|
| Top of column | 10–20 | 20–25 | 50–60 | 0 |
| Bottom | 91–93 | 1–3 | 1–2 | 1–1.5 |

Hydrogenation was performed using a 5% Pd/C catalyst K-0227 from Heraeus which, once hydrogenation was complete, was removed by filtration through two catalyst filters and employed for the next batch. The total of 5 kg of catalyst which had been employed were still fully active at the end of the campaign.

| Hydrogenation conditions: | |
|---|---|
| 1st phase hydrogenation: | 80° C. until $H_2$ was no longer taken up |
| 2nd phase hydrogenation: | 1 hour at 150° C. |
| Hydrogenation pressure: | 10 bar |
| ACEOM feed: | 5000 kg |

The methyl 2-acetyloctanoate which was obtained after the catalyst had been filtered off was then distilled continuously.

| Top-of-column temperature: | 135–145° C. |
|---|---|
| Bottom temperature: | 180–185° C. |
| Vacuum: | 50–9 mbar |
| Yields: | (Σ batch 1–7) 19850 kg (= 81% of theory based on hexanal) |
| Purity: | 99.2% |

EXAMPLE 3

Batch 1:

348.4 g of methyl acetoacetate (3.00 mol) and 300.5 g of hexanal (3.00 mol) were introduced into a 2-liter reaction vessel, the mixture being cooled to 5° C. 1.5 g of piperidine (0.018 mol) were metered in with cooling and stirring in the course of 15 minutes, and stirring was continued for 2 hours at 30° C.

The water of reaction formed and unreacted hexanal and acetoacetate were then distilled using a thin-film distillation apparatus.

(Heating temperature: 130° C., pressure 20 mbar, distillate temperature: 82–89° C.).

This gave 367.1 g of methyl 2-acetyl-2-octenoate as bottom product and 274.6 g of unreacted starting materials and water of reaction in the distillate.

The bottom product (methyl 2-acetyl-2-octenoate) was introduced into a 1-liter stirred autoclave, treated with 0.3 g of 5% palladium/active charcoal as the catalyst and hydrogenated for 10 minutes at 90° C.

The reaction mixture was then cooled to room temperature, the catalyst was filtered off, and the filtrate was distilled at 1 mbar over a Vigreux column (length 15 cm, diameter: 3 cm) equipped with distillation bridge.

| First runnings (79–82° C.): | 7.8 g |
|---|---|
| Main fraction (82–90° C.): | 340.1 g (=56.7% of theory), 97.9 area % (GC) |
| Bottom product: | 18.6 g |

Batch 2:

The reaction was carried out and the unreacted starting materials and the water of reaction were distilled off analogously to batch 1.

This gave 370.6 g of methyl acetyloctenoate as bottom product and 277.2 g of unreacted starting materials and water of reaction in the distillate.

The hydrogenation and the removal of the catalyst were carried out analogously to batch 1, as was the distillation.

| Quantities: | |
|---|---|
| First runnings (79–82° C.): | 10.2 g |
| Main fraction (82–90° C.): | 335.5 g (55.9% of theory), 98.2 area % (GC) |
| Bottom product: | 16.9 g |

Batch 3

The reaction was carried out and the unreacted starting materials and the water of reaction were distilled off analogously to batch 1.

This gave 384.2 g of methyl acetyloctenoate as bottom product and 257.8 g of unreacted starting materials and water of reaction in the distillate.

The hydrogenation and the removal of the catalyst were carried out analogously to batch 1, as was the distillation.

| First runnings (79–82° C.): | 6.5 g |
|---|---|
| Main fraction (82–90° C.): | 345.8 g (57.6% of theory), 98.4 area % (GC) |
| Bottom product: | 18.3 g |

Batch 4 (Use of the unreacted starting materials from batches 1–3 which had been distilled off, after the aqueous phase had been separated off by means of phase separation)

235.0 g of organic phase from distillate (batch 1)+
236.6 g of organic phase from distillate (batch 2)+
216.5 g of organic phase from distillate (batch 3) were introduced into a 2-liter reaction vessel, the mixture being cooled to 5° C. 1.6 g of piperidine (0.019 mol) were metered in with cooling and stirring in the course of 15 minutes, and stirring was continued for 2 hours at 30° C.

The water of reaction formed and unreacted hexanal and acetoacetate were then distilled using a thin-film distillation apparatus.

(Heating temperature: 13° C., pressure 20 mbar, distillate temperature: 82–89° C.).

This gave 480.5 g of methyl acetyloctenoate as the bottom product and 198.9 g of unreacted starting materials and water of reaction in the distillate.

The hydrogenation and the removal of the catalyst were carried out analogously to batch 1, as was the distillation.

| | |
|---|---|
| First runnings (79–82° C.): | 13.6 g |
| Main fraction (82–90° C.): | 429.5 g, 98.2 area % (GC) |
| Bottom product: | 31.4 g |
| Yield (batches 1–4): | 1451 g (=80.6% of theory) |
| Purity (GC area %): | 98.1% |

We claim:

1. A process for the preparation of a 2-acetylcarboxylic ester by reacting an acetoacetic ester with an aldehyde, followed by hydrogenation, which comprises
   a) reacting an acetoacetic ester having 1 to 6 C atoms in the alkyl moiety with an aliphatic aldehyde having 1 to 12 C atoms at 0 to 40° C. in the presence of a condensation catalyst,
   b) removing, after condensation, the water of reaction formed and unreacted starting materials from the reaction mixture, subsequently
   c) hydrogenating the remaining residue in substance at 20 to 160° C. and a pressure of 1 to 100 bar in the presence of a hydrogenation catalyst, the temperature in the first hydrogenation phase being between 20 and 90° C. and the temperature in the second phase being increased to 50 to 160° C., depending on the starting temperature,
   d) and subsequently isolating the 2-acetyl-carboxylic ester in question from the reaction mixture by distillation.

2. The process as claimed in claim 1, wherein an acetoacetic ester having 1 to 3 C atoms in the alkyl moiety is employed.

3. The process as claimed in claim 1, wherein the aldehyde employed is a straight-chain, branched or cyclic aldehyde which can be saturated or mono- or polyunsaturated and which is unsubstituted or substituted by groups which are inert under the reaction conditions.

4. A process as claimed in claim 2, wherein the aldehyde employed is an aliphatic saturated aldehyde having 2 to 10 C atoms.

5. The process as claimed in claim 1, wherein the condensation catalyst employed is ammonia, piperidine, pyridine, substituted pyridines, morpholine, diethylamine, diethanolamine or salts of these with organic acids.

6. The process as claimed in claim 1, wherein the water of reaction and unreacted starting materials are distilled off continuously.

7. The process as claimed in claim 1, wherein step c) is carried out at 5 to 30 bar.

8. The process as claimed in claim 1, wherein the second hydrogenation phase is carried out at 80 to 150° C.

* * * * *